(12) United States Patent
Huang et al.

(10) Patent No.: US 11,278,217 B2
(45) Date of Patent: Mar. 22, 2022

(54) TRANSDERMAL MICRONEEDLE ARRAY PATCH

(71) Applicants: RichHealth Technology Corporation, Zhubei (TW); Richtek Technology Corporation, Chupei (TW)

(72) Inventors: Jung-Tang Huang, Zhubei (TW); Kuan-Ting Lee, Zhubei (TW); Dahong Qian, Boston, MA (US)

(73) Assignee: RICHHEALTH TECHNOLOGY CORPORATION

( * ) Notice: Subject to any disclaimer, the term of this patent is extended or adjusted under 35 U.S.C. 154(b) by 821 days.

(21) Appl. No.: 15/939,772

(22) Filed: Mar. 29, 2018

(65) Prior Publication Data

US 2018/0279929 A1  Oct. 4, 2018

Related U.S. Application Data

(60) Provisional application No. 62/479,603, filed on Mar. 31, 2017.

(30) Foreign Application Priority Data

Mar. 7, 2018 (TW) .................................. 107107686

(51) Int. Cl.
| | |
|---|---|
| *A61B 5/145* | (2006.01) |
| *A61B 5/15* | (2006.01) |
| *A61B 5/1486* | (2006.01) |
| *A61B 5/00* | (2006.01) |
| *A61M 37/00* | (2006.01) |

(52) U.S. Cl.
CPC ...... *A61B 5/14514* (2013.01); *A61B 5/14532* (2013.01); *A61B 5/14865* (2013.01); *A61B 5/150022* (2013.01); *A61B 5/150267* (2013.01); *A61B 5/150969* (2013.01); *A61B 5/150984* (2013.01); *A61B 5/685* (2013.01); *A61B 5/14546* (2013.01); *A61B 5/150442* (2013.01); *A61B 5/6833* (2013.01); *A61M 37/0015* (2013.01)

(58) Field of Classification Search
CPC ............ A61B 5/14514; A61B 5/14546; A61B 5/14865; A61B 5/150984; A61B 5/6833; A61B 5/685; A61M 37/0015
See application file for complete search history.

(56) References Cited

U.S. PATENT DOCUMENTS

| | | | |
|---|---|---|---|
| 10,034,626 B2 * | 7/2018 | Huang | A61B 5/685 |
| 2007/0123770 A1 * | 5/2007 | Bouton | A61B 5/0537 600/407 |
| 2010/0324392 A1 * | 12/2010 | Yee | G06K 7/10366 600/345 |
| 2017/0246440 A1 * | 8/2017 | Kalghatgi | A61L 2/14 |

* cited by examiner

*Primary Examiner* — Puya Agahi
(74) *Attorney, Agent, or Firm* — Behmke Innovation Group; James M. Behmke; Jonathon P. Western

(57) ABSTRACT

Provided is a transdermal microneedle array patch, including: a bottom cover; a top cover; a substrate disposed within the top cover; and a first probe and a second probe disposed between the bottom cover and the top cover and electrically connected the substrate. The first and second probes form an open circuit. While the bottom cover is combined with the top cover to form the transdermal microneedle array patch, the first and second probes form a closed circuit.

15 Claims, 9 Drawing Sheets

TRANSDERMAL MICRONEEDLE ARRAY PATCH

CROSS-REFERENCE RELATED APPLICATION

The present disclosure claims the benefit of U.S. Provisional Application No. 62/479,603, filed on Mar. 31, 2017, and Taiwan Application No. 107107686, filed Mar. 7, 2018, which are hereby incorporated by reference as if they are fully set forth herein.

BACKGROUND OF THE INVENTION

1. Technical Field

The present disclosure relates to a transdermal microneedle array patch, and more particularly, to a disposable transdermal microneedle array patch.

2. Description of Related Art

Human interstitial fluid mainly flows in the hypodermis. Interstitial fluid is rich in amino acids, fatty acids, sugar, salts, hormones, coenzymes, waste produced by cells, etc. Therefore, by analyzing the concentrations of the substances in the interstitial fluid, the physiological condition can be effectively determined.

In addition, when a medication is taken or administered, for example, it is slowly released in the interstitial fluid, and thus its concentration varies over time. Therefore, by analyzing the concentration of the drug in the interstitial fluid, the effectiveness of the medication can be effectively monitored.

Most physiology test equipment (e.g., transdermal sensors) available today requires the use of a needle to penetrate the cuticular layer for extracting the interstitial fluid for subsequent analysis and detection. The low-invasive puncturing of such a transdermal sensor effectively alleviates pain experienced by a user while collecting the interstitial fluid.

However, existing physiology test equipment is often not durable. For example, transdermal sensors can be used for a single test. A new transdermal sensor will need to be used for another test. Moreover, data detected are transmitted directly to a reader or a mobile phone, and will not be stored in the transdermal sensor itself. Further, current physiology test equipment requires continuous testing; that is, testing cannot be interrupted and then resumed. Therefore, system power may be wasted, and the frequent replacement of the transdermal sensors is also a waste of resources.

SUMMARY OF THE INVENTION

One of the main objectives of the present disclosure is to provide a transdermal microneedle array patch, which includes: a bottom cover; a top cover; a substrate disposed within the top cover; and a first probe and a second probe disposed between the top cover and the bottom cover and electrically connected with the substrate, wherein the first and second probes form an open circuit, and when the bottom cover is combined with the top cover to form the transdermal microneedle array patch, the first and second probes form a closed circuit.

By designing the bottom and top covers of the transdermal microneedle array patch according to the present disclosure to be detachable with respect to each other, the microneedle group collection is provided on the bottom cover, while the signal processing unit and the power supply unit are provided on the top cover. Upon combining the bottom and top covers, the first and second probes form a closed loop to turn on the signal processing unit, such that the microneedle group collection obtains a suitable voltage to enable an analyte in the subcutaneous interstitial fluid to electrochemically react with enzymes on the microneedle group collection, and electrical signals resulting from the reaction are subsequently read by the signal processing unit. Users can easily replace the bottom cover including the microneedle group collection without the need to replace the top cover including the signal processing unit and the power supply unit in the case of long-term monitoring. Accordingly, test interruptions are avoided. Moreover, data loss due to replacement of the signal processing unit can be eliminated. Also, the turn-on time can be adjusted as needed to conserve system power.

DETAILED DESCRIPTION OF THE EMBODIMENTS

The implementations of present disclosure are described by the following specific embodiments. One of ordinary skill in the art can readily understand the advantages and effects of the present disclosure upon reading the disclosure of this specification. However, the embodiments of the present disclosure are by no means meant to limit the present disclosure; the present disclosure may also be practiced or applied in other different implementations.

Figure 1:
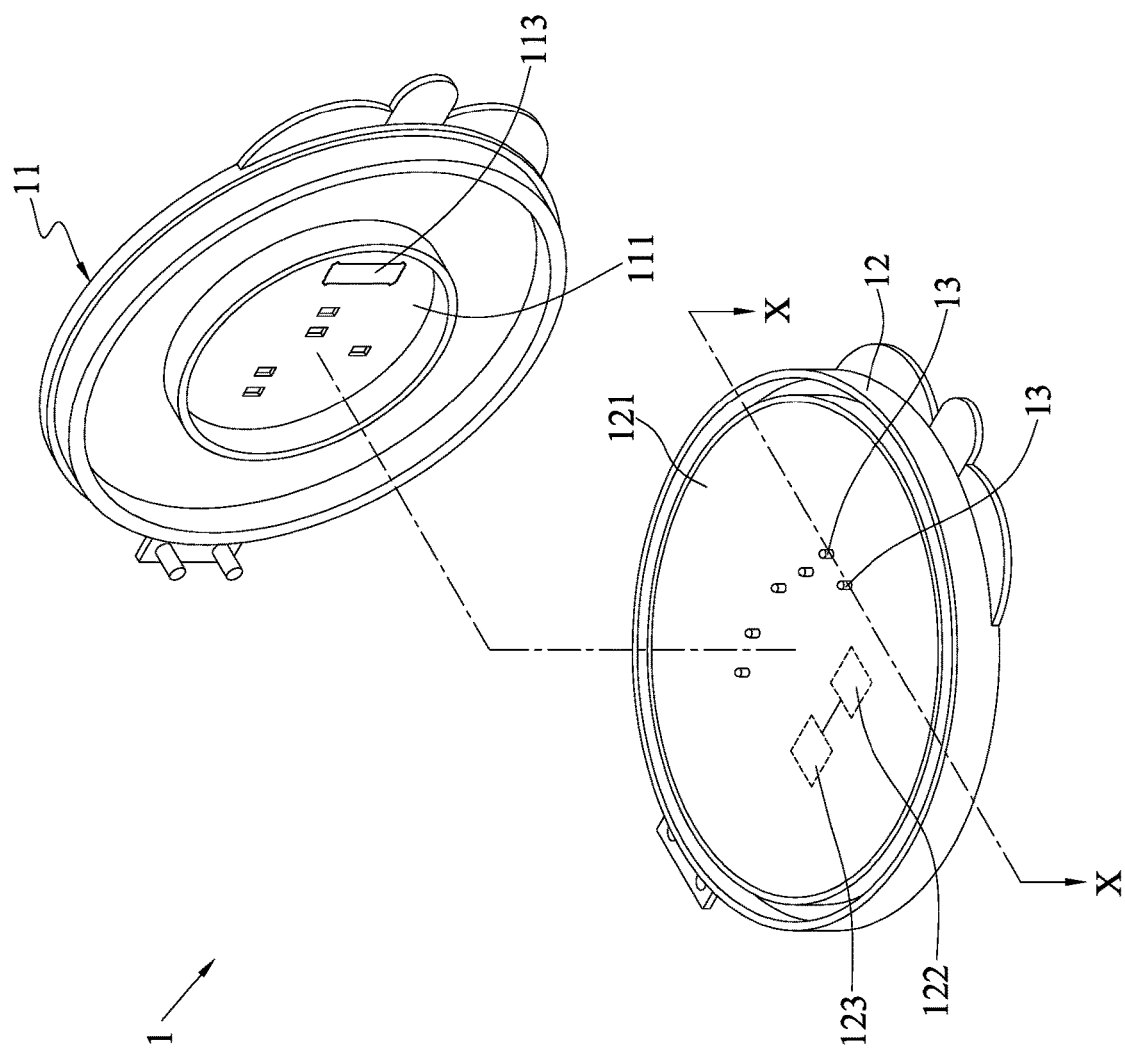
FIG. 1 is a schematic diagram depicting the assembly of a transdermal microneedle array patch in accordance with an embodiment of the present disclosure.
Figure 2:
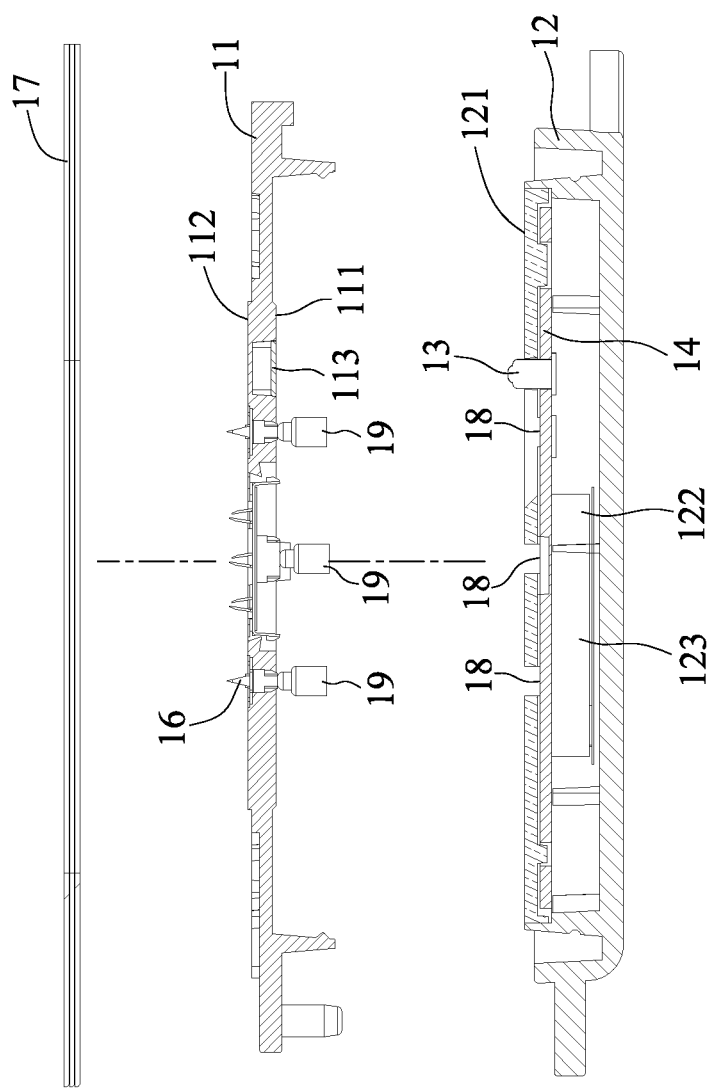
FIG. 2 is a cross-sectional view of the transdermal microneedle array patch in accordance with the embodiment of the present disclosure.
Figure 3:
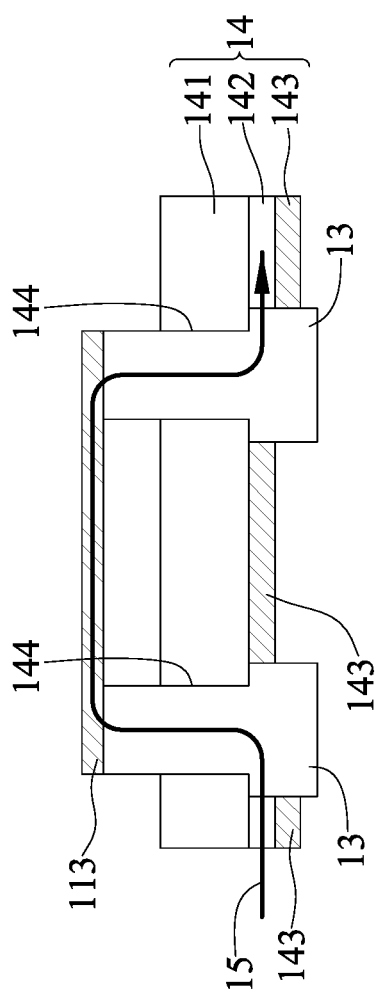
FIG. 3 is a cross-sectional view of a substrate in FIG. 1 taken along a line segment X-X.

Referring to FIGS. 1, 2 and 3, a transdermal microneedle array patch 1 according to the present disclosure includes a bottom cover 11 and a top cover 12. The bottom cover 11 has a first surface 111 and a second surface 112 opposite to the first surface 111. A metal sheet 113 is provided on the first surface 111. A substrate 14 is disposed within the top cover 12, and has two probes 13 protruded from an inner surface 121 of the top cover 12, wherein the two probes 13 form an open circuit.

In an embodiment, the two probes 13 are not both disposed on the substrate 14. For example, one probe 13 is provided on the substrate 14, while the other probe 13 is provided on the metal sheet 113, and the two probes 13 are electrically connected with the substrate 14. The present disclosure is not limited thereto.

In an embodiment, as shown in FIG. 3, the substrate 14 includes a dielectric layer 141, and a circuit layer 142 formed on the dielectric layer 141. Openings 144 are formed in the dielectric layer 141 and protrude therethrough, such that the two probes 13 are allowed to be inserted into the openings 144. In other words, the two probes 13 penetrate the dielectric layer 141 and are disposed therein. In an embodiment, one end of each of the two probes 13 is protruded from a surface of the dielectric layer 141 to be electrically connected with the circuit layer 142, whereas the other end of each of the two probes 13 is protruded from another surface of the dielectric layer 141 to be further protruded from the inner surface 121 of the top cover 12, as shown in FIG. 2. The substrate 14 further includes an insulating layer 143. The insulating layer 143 is formed on the circuit layer 142, and also on a portion of the dielectric layer 141 that is free from the formation of the circuit layer 142.

The transdermal microneedle array patch 1 according to the present disclosure further includes a microneedle group collection 16 provided on the second surface 112 of the bottom cover 11. The microneedle group collection 16 is used to be placed against a user's skin 17.

A signal processing unit 122 and a power supply unit 123 may be further provided within the top cover 12. The signal processing unit 122 is electrically connected with the two probes 13 via the circuit layer 142. The power supply unit 123 provides operating power to the signal processing unit 122.

When the bottom cover 11 is combined with the top cover 12 to form the transdermal microneedle array patch 1, the metal sheet 113 of the bottom cover 11 comes into contact with the two probes 13 protruded from the inner surface 121 of the top cover 12, allowing the two probes 13 to form a closed circuit; that is, a current path 15 is formed and the signal processing unit 122 is turned on accordingly. In an embodiment, electrical signals of the microneedle group collection 16 may be electrically connected with electrical contacts 18 of the signal processing unit 122 via conductive pillars 19, thereby obtaining a suitable electrochemical reaction voltage, which interacts with an analyte in the interstitial fluid to generate a current/voltage signal. This current/voltage signal is transmitted to the signal processing unit 122 to be acquired and analyzed for determining the concentration of the analyte. This sensed signal may be stored in a storage unit (not shown) in the top cover 12.

In an embodiment, the two probes 13 may form a closed circuit without the use of the metal sheet 113. For example, the two probes 13 may be forced to come into contact with each other to form a closed circuit with exertion of the bottom cover 11.

When using the transdermal microneedle array patch 1 according to the present disclosure, a user first places the bottom cover 11 provided with the microneedle group collection 16 against his/her skin, and then combines the top cover 12 with the bottom cover 11 to enable the electrical connection of the two probes via the metal sheet 113, thus turning on the signal processing unit 122 in order to measure the concentrations of the various substances in the subcutaneous interstitial fluid. Since the bottom cover 11 and the top cover 12 are detachable with respect to each other, when the microneedle group collection 16 needs replacing, the user may first remove the top cover 12, and replace the bottom cover 11 including the microneedle group collection 16 with another bottom cover 11 including a new microneedle group collection 16 before placing it against the skin 17. The original top cover 12 is assembled onto the new bottom cover 11, such that the user does not need to replace the top cover 12 including the signal processing unit 122. Through such a structural design, as shown in FIG. 1, the bottom cover 11 and the top cover 12 are easily assembled together via an annular groove and a corresponding annular flange provided respectively thereon, and secured together with a latch. It is to be noticed that the present disclosure is not limited thereto. In other words, the microneedle group collection 16 and the circuits inside the top cover 12 according to the present disclosure may be separated, so that the transdermal microneedle array patch 1 can be reused by simply replacing just the microneedle group collection 16 without discarding the entire device, thereby achieving easy replacement and power saving. The present disclosure is also suitable for long-term monitoring, and physiological signals detected by different bottom cover 11 may all be stored in the same top cover 12 to avoid data loss. In addition, since the top cover 12 is not replaced, resources are conserved.

Figure 4:
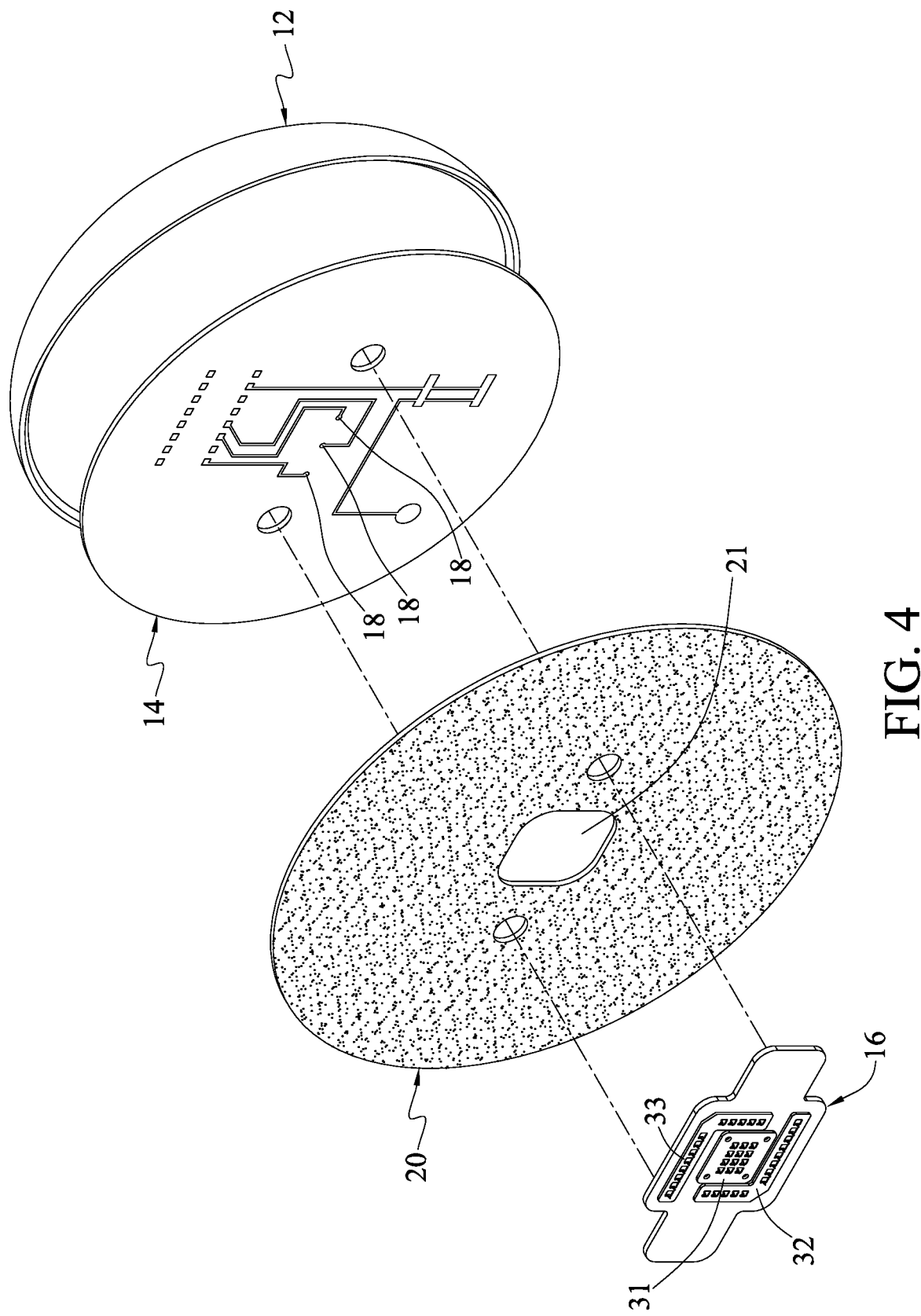
FIG. 4 is a front view of the assembly of a transdermal microneedle array patch in accordance with another embodiment of the present disclosure.
Figure 5:
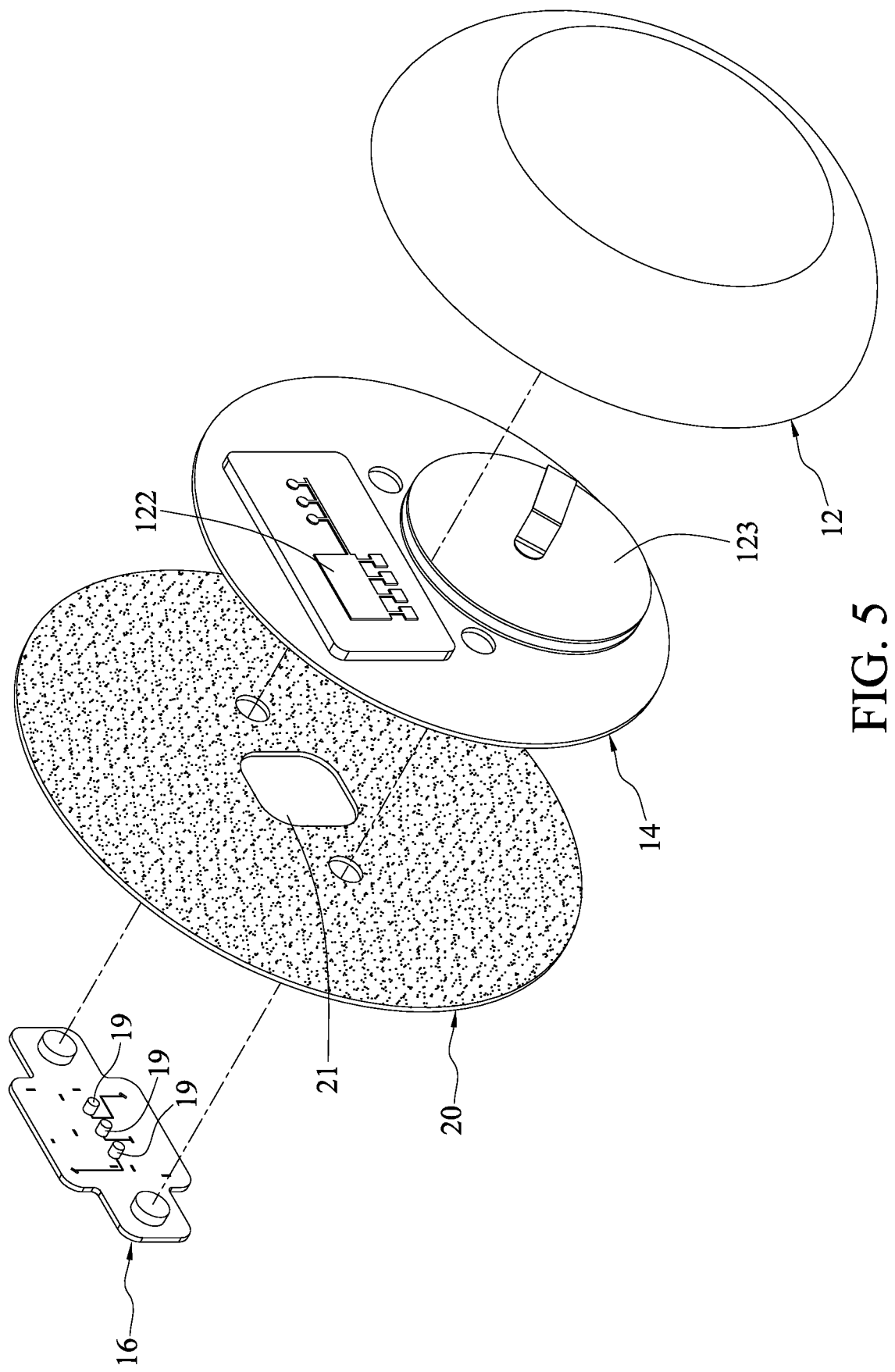
FIG. 5 is a rear view of the assembly of a transdermal microneedle array patch in accordance with another embodiment of the present disclosure.

Referring to FIGS. 4 and 5, the microneedle group collection 16 of the transdermal microneedle array patch 1 according to the present disclosure is electrically connected with the electrical contacts 18 of the signal processing unit 122 on the substrate 14 via the conductive pillars 19. In this embodiment, the signal processing unit 122 and the power supply unit 123 are provided on the same surface of the substrate 14, whereas the electrical contacts 18 is provided on another surface of the substrate 14. A flexible pad 20 may be further provided between the microneedle group collection 16 and the substrate 14. An opening is provided in the flexible pad 20 to enable the conductive pillars 19 of the microneedle group collection 16 to pass through. Owing to the flexible pad 20 included in the transdermal microneedle array patch 1 according to the present disclosure, the transdermal microneedle array patch 1 may be snugly adhered to the user conforming to the muscle profile of the user.

In an embodiment, the microneedle group collection 16 further includes a first microneedle group 31, a second microneedle group 32, and a third microneedle group 33, wherein the first microneedle group 31 are used as working electrodes, the second microneedle group 32 as reference electrodes, and the third microneedle group 33 as counter electrodes. A more detailed illustration on the structure of the microneedle group collection 16 is provided below with reference to FIG. 6.

In an embodiment, the first microneedle group 31 is formed by stacking a first sheet 311, a second sheet 312, and a third sheet 313. The first sheet 311 is formed with at least one first through hole 3111 and at least one first spur 3112 is provided at an edge of the first through hole 3111. Similarly, the second sheet 312 is formed with at least one second through hole 3121 and a second spur 3122 is provided at an edge of the second through hole 3121. The third sheet 313 is formed with at least one third through hole 3131 and at least one third spur 3132 is provided at an edge of the third through hole 3131. The third sheet 313 is interposed between the first sheet 311 and the second sheet 312. The first sheet 311, the second sheet 312, and the third sheet 313 are stacked together in such a way that the second spur 3122 of the second sheet 312 passes through the third through hole 3131 of the third sheet 313 and the first through hole 3111 of the first sheet 311, and the third spur 3132 of the third sheet 313 passes through the first through hole 3111 of the first sheet 311, allowing the first spur 3112, the second spur 3122, and the third spur 3132 to form a triangular cone.

In addition, a hook 3123 may be provided on an edge of the second sheet 312 to be secured with a corresponding cavity (not shown) on the circuit board. In an embodiment, a conductive tab 3124 is provided on an edge of the second sheet 312 to be inserted onto the circuit board in order to be electrically connected with a conductive pillar 19.

Similarly, the second microneedle group 32 includes a sheet 321 with at least one through hole 3211 provided thereon. A spur 3212 is provided on an edge of the through hole 3211. In addition, a hook 3213 is provided on an edge of the sheet 321 to be secured with a corresponding cavity on the circuit board. A conductive tab 3214 is provided on an edge of the sheet 321 to be inserted onto the circuit board in order to be electrically connected with a conductive pillar 19.

Similarly, the third microneedle group 33 includes a sheet 331 with at least one through hole 3311 provided thereon. A spur 3312 is provided on an edge of the through hole 3311. In addition, a hook 3313 is provided on an edge of the sheet 331 to be secured with a corresponding cavity on the circuit board. A conductive tab 3314 is provided on an edge of the sheet 331 to be inserted onto the circuit board in order to be electrically connected with a conductive pillar 19.

Figure 6:
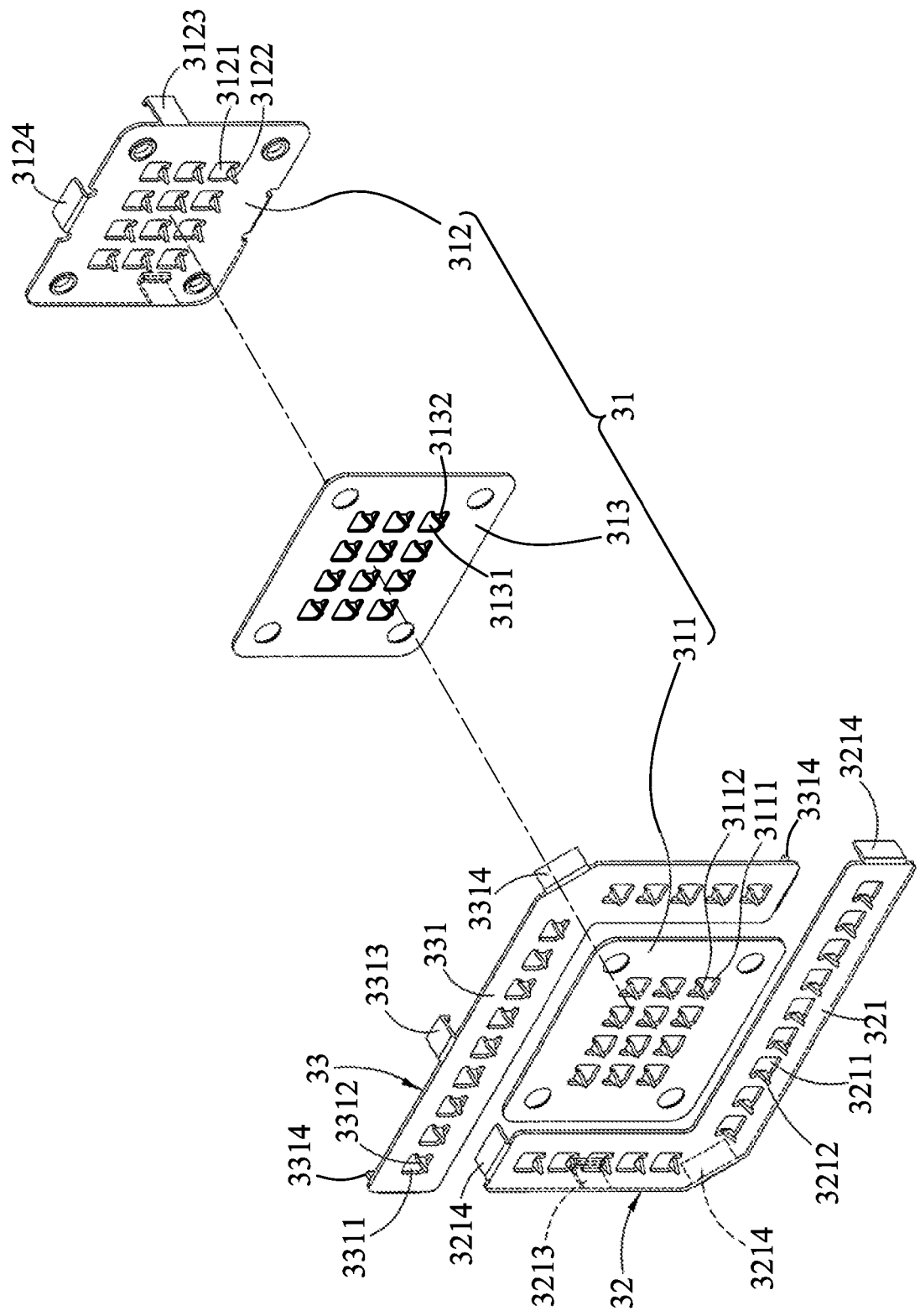
FIG. 6 is a schematic diagram depicting a microneedle group collection in the transdermal microneedle array patch in accordance with an embodiment of the present disclosure.

In an embodiment, the quantity of the first through hole 3111, the second through hole 3121, and the third through hole 3131 are commensurate with each other and plural. The first through hole 3111, the second through hole 3121, and the third through hole 3131 may be arranged in an array. For example, as shown in FIG. 6, the number of the first, second, and third through holes each is 12 and are arranged in a 3×4 matrix. However, the present disclosure does not limit the number of through holes and the arrangement of the array as such. In addition, the first spurs 3112, the second spurs 3122, and the third spurs 3132 have commensurate quantities with the first through holes 3111, the second through holes 3121, and the third through holes 3131, respectively.

In an embodiment, each spur of the first microneedle group 31, the second microneedle group 32, and the third microneedle group 33 may be formed by stamping or an etching process. The spurs may be made of materials selected from stainless steel, nickel, nickel alloy, titanium, titanium alloy, carbon nanotube, silicon material, and resin. Biocompatible metals (e.g., gold or palladium) are deposited on the surfaces of the spurs. Resin may be, for example, polycarbonate, polymethacrylic acid copolymer, ethylene/vinyl acetate copolymer, Teflon (polytetrafluoroethylene), or polyester. The height of the spurs may be between 300 and 600 micron; the width of the base of the spurs may be between 150 and 450 micron; and the interval between the tips of the spurs may be between 500 and 3000 micron.

Figure 7:
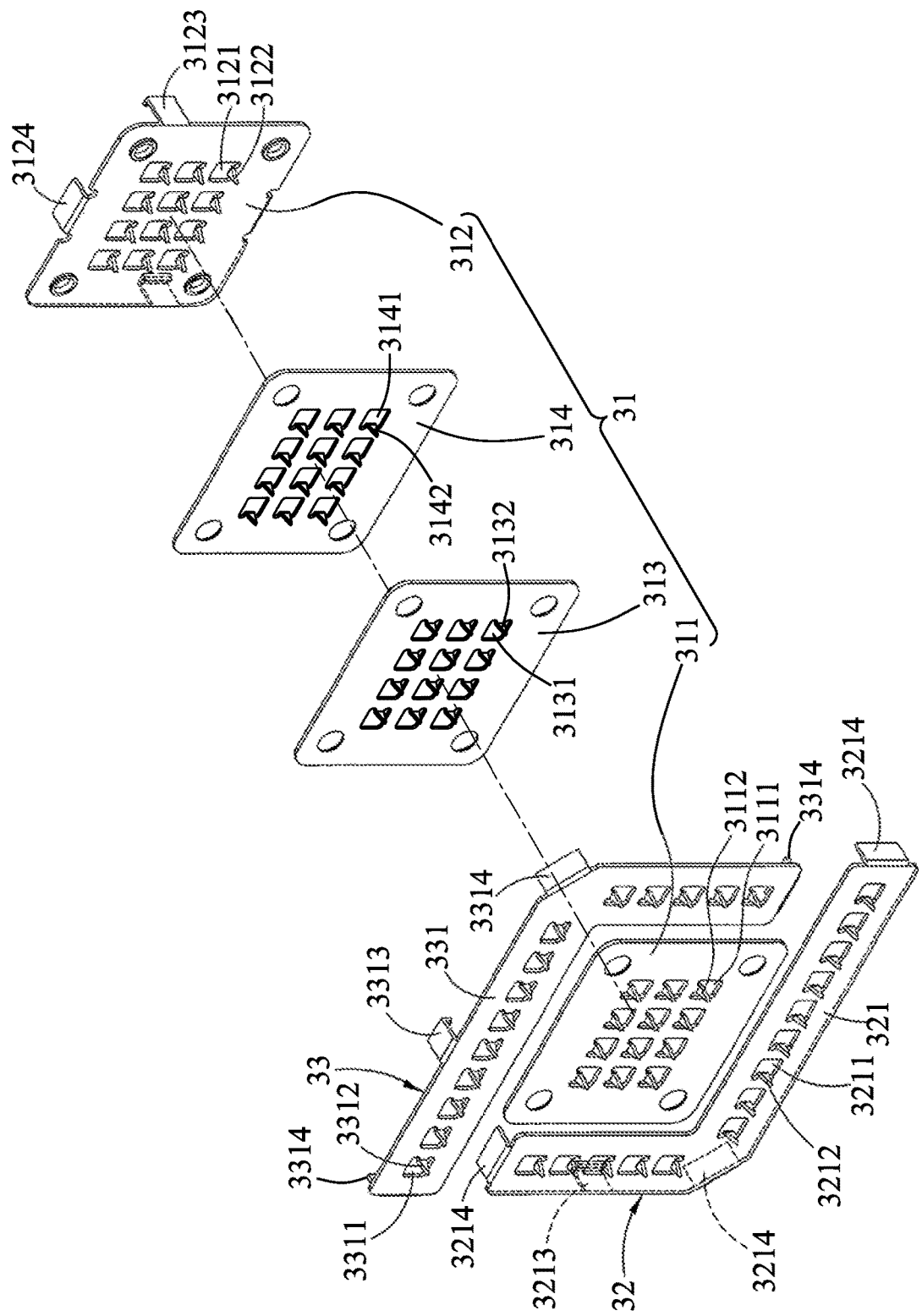
FIG. 7 is a schematic diagram depicting a microneedle group collection in the transdermal microneedle array patch in accordance with another embodiment of the present disclosure.

FIG. 7 is another embodiment of the microneedle group collection 16 according to the present disclosure. In this embodiment, elements which are the same as those depicted in the previous embodiments are not repeated for conciseness. In this embodiment, the first microneedle group 31 is formed by stacking a first sheet 311, a second sheet 312, a third sheet 313, and a fourth sheet 314 together. The first sheet 311 is formed with at least one first through hole 3111 and at least one first spur 3112 is provided at an edge of the first through hole 3111. The second sheet 312 is provided with at least one second through hole 3121 and a second spur 3122 provided at an edge of the second through hole 3121. The third sheet 313 is formed with at least one third through hole 3131 and at least one third spur 3132 is provided at an edge of the third through hole 3131. The four sheet 314 is formed with at least one fourth through hole 3141 and at least one third spur 3142 is provided at an edge of the third through hole 3141. The third sheet 313 and the fourth sheet 314 are provided between the first sheet 311 and the second sheet 312. The first sheet 311, the second sheet 312, the third sheet 313, and the fourth sheet 314 are stacked together in such a way that the second spur 3122 of the second sheet 312 passes through the fourth through hole 3141 of the fourth sheet 314, the third through hole 3131 at the respective location on the third sheet 313, and the first through hole 3111 at the respective location on the first sheet 311; the fourth spur 3142 of the fourth sheet 314 passes through the third through hole 3131 of the third sheet 313 and the first through hole 3111 of the first sheet 311; and the third spur 3132 of the third sheet 313 passes through the first through hole 3111 of the first sheet 311, allowing the first spur 3112, the second spur 3122, the third spur 3132, and the fourth spur 3142 to form a square pyramid.

In an embodiment, the quantity of the first through hole 3111, the second through hole 3121, the third through hole 3131, and the fourth through hole 3141 are commensurate with each other and plural. The first through hole 3111, the second through hole 3121, the third through hole 3131, and the fourth through hole 3141 may be arranged in an array. For example, as shown in FIG. 7, the number of the first, second, third, and fourth through holes each is 12 and arranged in a 3×4 matrix. However, the present disclosure does not limit the number of through holes and the arrangement of the array as such. In addition, the first spurs 3112, the second spurs 3122, the third spurs 3132, and the fourth spurs 3142 have commensurate quantities with the first through holes 3111, the second through holes 3121, the third through holes 3131, and the fourth through holes 3141, respectively.

In another embodiment of the microneedle group collection 16 according to the present disclosure, the first microneedle group 31 is formed by stacking only a first sheet 311 and a second sheet 312 together. The present disclosure does not limit the number of sheets forming the first microneedle group 31. The detailed illustrations of the first sheet 311 and the second sheet 312 of this embodiment are the same as those described before, and will not be repeated.

In the above four embodiments, each spur 3112, 3122, 3132, 3142 of the first microneedle group 31 includes a tapering portion and a base, wherein the through hole a sheet enables spurs on the edges of through holes of the rest of the sheets to pass through, with the tips of the tapering portions not at the same height. In another embodiment of the present disclosure, the spurs are designed in advance with different heights based on the order in which they are stacked, such that after the spurs on the edges of the through holes of the rest of the sheets pass through the through hole of the sheet on the top, the tips of the tapering portions of the respective sheets are at the same height.

The surface of each spur of the microneedle group collection 16 in the transdermal microneedle array patch 10 according to the present disclosure may be modified according to the analyte to be measured. The analyte may be a biomolecule, such as blood sugar, cortisol, fatty acid, lactic acid, etc. The analyte may also be a drug molecule, such as an antibiotic. Thus, the inner surface of each of the spurs of the first microneedle group 31 of the microneedle group collection 16 may be coated with a sensing polymer, such as an antibody, an aptamer, a recombinant monomer, carbohydrate, glucose oxidase or hydroxybutyrate dehydrogenase, while the outer surface of each of the spurs may be coated with anti-skin allergy drug. For example, when measuring blood sugar, glucose oxidase may be attached to the inner surface of each of the spurs. The typical attachment of an antibody or an aptamer includes applying a self-assemble monolayer (SAM) on a gold surface layer of each of the spurs of the first microneedle group 31 used as the working electrodes, followed by the attachment of the antibody or the aptamer and then the application of blocking molecules to fill the areas of the SAM where the antibody or the aptamer are not attached, thereby ensuring the specificity. Carbon nanotubes may be further mixed in the gold surface layer to increase sensitivity.

Figure 8:
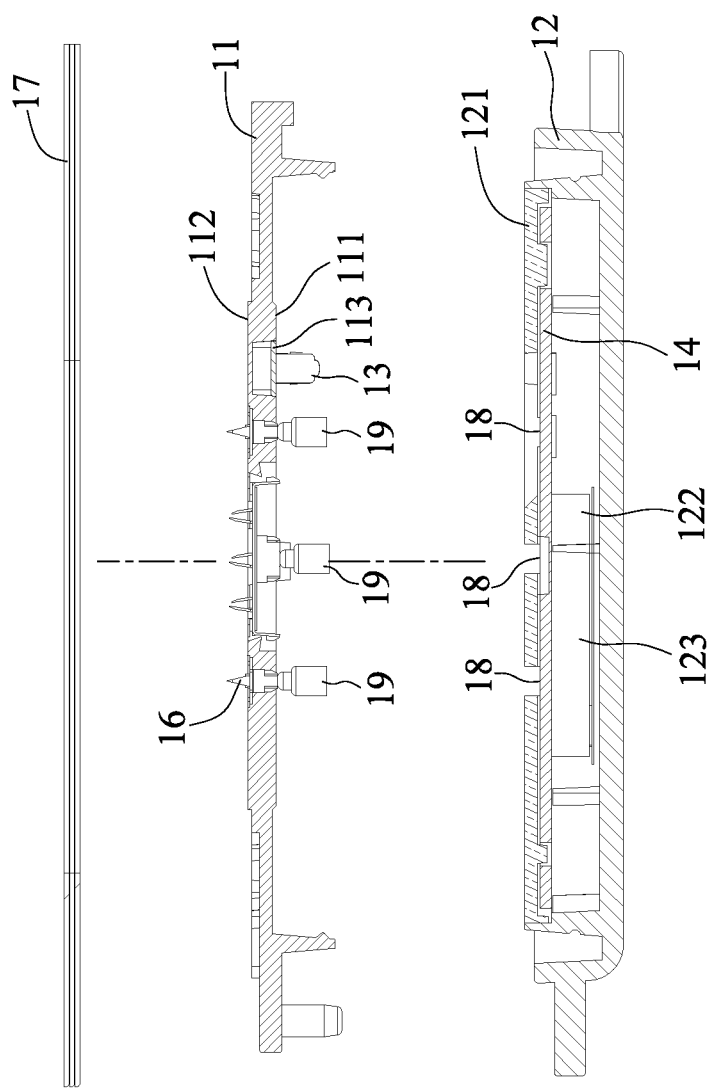
FIG. 8 is a cross-sectional view of a transdermal microneedle array patch in accordance with still another embodiment of the present disclosure.
Figure 9:
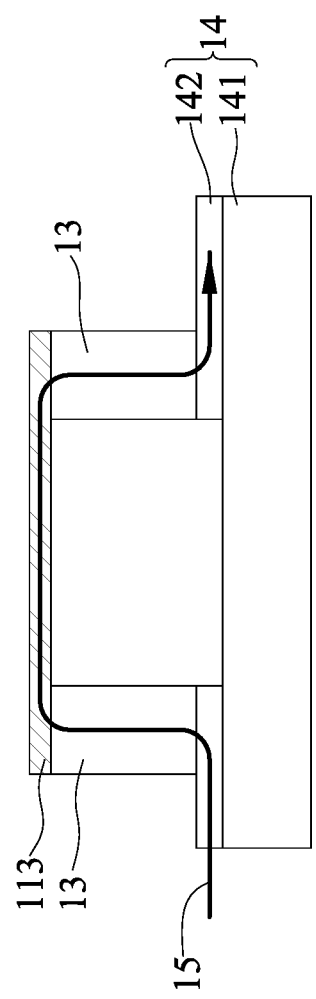
FIG. 9 is a cross-sectional view of a substrate in FIG. 8.

Referring to FIGS. 8 and 9, another embodiment of the transdermal microneedle array patch according to the present disclosure is shown. Compared to the previous embodiments, only the locations of the probes 13 are different, while the rest of the technical content are the same and will not be repeated. Only the differences are depicted below.

As shown in FIGS. 8 and 9, two probes 13 are provided on the metal sheet 113 rather than on the substrate 14. The substrate 14 provided within the top cover 12 includes the dielectric layer 141 and the circuit layer 142 formed on the dielectric layer 141, wherein an open circuit is formed in the circuit layer 142.

In an embodiment, the two probes 13 are not both provided on the metal sheet 113, but are both provided on the circuit layer 142, or one probe 13 is provided on the circuit layer 142 and the other probe 13 is provided on the metal sheet 113. When both of the probes 13 are disposed on the circuit layer 142, they may come into contact under pressure from the bottom cover 11 to form a closed circuit, and thus eliminating the need of the metal sheet 113. However, the present disclosure is not limited as such.

When the bottom cover 11 is assembled with the top cover 12 to form the transdermal microneedle array patch 1, the two probes 13 are in contact with the circuit layer 142. The circuit layer 142 is provided with a closed circuit formed by the two probes 13 and the metal sheet 113, thereby creating a current path 15 and turning on the signal processing unit 122.

The above embodiments are only used to illustrate the principles of the present disclosure, and should not be construed as to limit the present disclosure in any way. The above embodiments can be modified by those with ordinary skill in the art without departing from the scope of the present disclosure as defined in the following appended claims.

What is claimed is:
1. A transdermal microneedle array patch, comprising:
a bottom cover;
a top cover;
a substrate disposed within the top cover, comprising:
 a dielectric layer having a first side and a second side corresponding to the first side; and
 a circuit layer formed on the first side of the dielectric layer; and
a first probe and a second probe penetrated through the dielectric layer, wherein each of the first and second probes has a first end and a second end corresponding to the first end, the first end is protruded from the first side of the dielectric layer and electrically connected with the circuit layer, and the second end is protruded from the second side of the dielectric layer, such that the first and second probes form an open circuit, and wherein when the bottom cover is combined with the top cover to form the transdermal microneedle array patch, the first and second probes form a closed circuit.

2. The transdermal microneedle array patch of claim 1, wherein the bottom cover includes a first surface and a second surface opposite to the first surface, and a metal sheet is provided on the first surface of the bottom cover and comes into contact with the first and second probes when the bottom cover is combined with the top cover to form the transdermal microneedle array patch, such that the first and second probes form the closed circuit.

3. The transdermal microneedle array patch of claim 2, wherein one of the first and second probes is disposed on the substrate and protruded from the top cover, and the other one of the first and second probes is disposed on the metal sheet of the bottom cover.

4. The transdermal microneedle array patch of claim 2, wherein the first and second probes are both disposed on the substrate and protruded from the top cover.

5. The transdermal microneedle array patch of claim 1, wherein when the bottom cover is combined with the top cover to form the transdermal microneedle array patch, and the first and second probes are forced to come into contact with each other to form the closed circuit under pressure from the bottom cover.

6. The transdermal microneedle array patch of claim 1, wherein the substrate further includes an insulating layer formed on the circuit layer and on a portion of the dielectric layer that is free from the formation of the circuit layer.

7. The transdermal microneedle array patch of claim 1, wherein the combination between the top and bottom covers is detachable.

8. The transdermal microneedle array patch of claim 1, further comprising a microneedle group collection disposed on the bottom cover and electrically connected with the substrate, a signal processing unit disposed within the top cover for generating a sensed signal when turned on when the first and second probes or the circuit layer form the closed circuit, and a power supply unit disposed within the top cover for providing an operating power to the signal processing unit.

9. The transdermal microneedle array patch of claim 8, wherein the microneedle group collection further includes a first microneedle group used as a working electrode, a second microneedle group used as a reference electrode, and a third microneedle group used as a counter electrode.

10. The transdermal microneedle array patch of claim 9, wherein the first microneedle group is formed by stacking at least two sheets together, each of the at least two sheets is provided with at least one through hole and at least one spur at an edge of the through hole, and the spur of one of the at least two sheets passes through the through hole of the other one of the at least two sheets, quantities of the spurs of the at least two sheets are commensurate with each other and plural, and the through holes of each of the at least two sheets are arranged in an array.

11. The transdermal microneedle array patch of claim 10, wherein the at least two sheets include a first sheet provided with at least one first through hole and at least one first spur provided at an edge of the first through hole, a second sheet provided with at least one second through hole and a second spur provided at an edge of the second through hole, and a third sheet provided with at least one third through hole and at least one third spur provided at an edge of the third through hole, such that, when the first, second and third sheets are stacked together, the second spur and the third spur pass through the first through hole of the first sheet and form a triangular cone with the first spur, quantities of the first through holes, the second through holes, and the third through holes are commensurate with each other and plural, and the plurality of the first through holes, the second through holes, and the third through holes are arranged in an array.

12. The transdermal microneedle array patch of claim 10, wherein the at least two sheets include a first sheet provided with at least one first through hole and at least one first spur provided at an edge of the first through hole, a second sheet provided with at least one second through hole and a second spur provided at an edge of the second through hole, a third sheet provided with at least one third through hole and at least one third spur provided at an edge of the third through hole, and a fourth sheet provided with at least one fourth through hole and at least one fourth spur provided at an edge of the third through hole, such that, when the first, second, third and fourth sheets are stacked together, the second spur, the third spur, and the fourth spur pass through the first through hole of the first sheet and form a square pyramid with the first spur, quantities of the first through holes, the second through holes, the third through holes, and the fourth through holes are commensurate with each other and plural, and the plurality of the first through holes, the second through holes, the third through holes, and the fourth through holes are arranged in an array.

13. The transdermal microneedle array patch of claim 10, wherein each of the spurs of the first microneedle group includes a tapering portion and a base, and the through hole of one of the sheets enables the spurs at the edges of through holes of the rest of the sheets to pass through, such that tips of the tapering portions are at or not at the same height.

14. The transdermal microneedle array patch of claim 10, wherein each of the spurs of the first microneedle group is formed by stamping or an etching process, and is made of a material selected from stainless steel, nickel, nickel alloy, titanium, titanium alloy, carbon nanotube, silicon material, and resin, and biocompatible metal is deposited on surfaces of the spurs.

15. The transdermal microneedle array patch of claim 10, wherein an inner surface of each of the spurs of the first microneedle group is coated with a sensing polymer, while an outer surface of each of the spurs is coated with anti-skin allergy drug, and the sensing polymer is an antibody, an aptamer, a recombinant monomer, carbohydrate, glucose oxidase, or hydroxybutyrate dehydrogenase.

* * * * *